(12) United States Patent
Oneda et al.

(10) Patent No.: US 6,461,294 B1
(45) Date of Patent: Oct. 8, 2002

(54) INFLATABLE MEMBER FOR AN ENDOSCOPE SHEATH

(75) Inventors: Katsumi Oneda, Alpine, NJ (US);
Edward Paul Harhen, Duxbury, MA (US)

(73) Assignee: Vision Sciences, Inc., Natick, MA (US)

( * ) Notice: Subject to any disclaimer, the term of this patent is extended or adjusted under 35 U.S.C. 154(b) by 79 days.

(21) Appl. No.: 09/702,155

(22) Filed: Oct. 30, 2000

(51) Int. Cl.$^7$ ............................................... A61M 5/00
(52) U.S. Cl. ...................................... 600/116; 606/194
(58) Field of Search .............................. 606/190, 194, 606/198, 153; 604/101.05, 509, 907, 919, 96.01, 523; 600/114, 116, 125, 121, 115, 123, 104

(56) References Cited

U.S. PATENT DOCUMENTS

| | | | |
|---|---|---|---|
| 4,066,070 A | 1/1978 | Utsugi | 128/4 |
| 4,148,307 A | 4/1979 | Utsugi | 128/4 |
| 4,176,662 A | 12/1979 | Frazer | 128/6 |
| 4,180,076 A | 12/1979 | Betancourt | 128/349 B |
| 4,224,929 A | 9/1980 | Furihata | 128/5 |
| 4,295,464 A | 10/1981 | Shihata | 128/1 R |
| 4,404,971 A | 9/1983 | LeVeen et al. | 128/348.1 |
| 4,676,228 A * | 6/1987 | Krasner et al. | 600/116 |
| 4,892,099 A * | 1/1990 | Ohkawa et al. | 606/194 |
| 5,025,778 A * | 6/1991 | Silverstein et al. | 600/104 |
| 5,078,681 A * | 1/1992 | Kawashima | 606/198 |
| 5,217,001 A * | 6/1993 | Nakao et al. | 600/123 |
| 5,331,947 A * | 7/1994 | Shturman | 600/115 |
| 5,569,161 A * | 10/1996 | Ebling et al. | 600/121 |
| 5,810,790 A * | 9/1998 | Ebling et al. | 604/523 |
| 5,876,329 A * | 3/1999 | Harhen | 600/125 |
| 6,007,482 A | 12/1999 | Madni et al. | 600/115 |
| 6,214,022 B1 * | 4/2001 | Taylor et al. | 606/153 |
| 6,234,958 B1 * | 5/2001 | Snoke et al. | 600/114 |
| 6,277,137 B1 * | 8/2001 | Chin | 606/190 |
| 6,344,028 B1 * | 2/2002 | Barry | 604/96.01 |

* cited by examiner

Primary Examiner—Teresa Walberg
Assistant Examiner—Leonid M Fastovsky
(74) Attorney, Agent, or Firm—Dorsey & Whitney LLP

(57) ABSTRACT

Apparatus and methods for attaching and forming enclosed inflatable members on an endoscope assembly with a disposable sheath are disclosed. In one embodiment, an apparatus includes a flexible and resilient cuff member that is positioned on the outer surface of the disposable sheath and sealably and fixedly bonded to the sheath cover material at the cuff edges to form an annular space capable of being inflated. The inflatable member formed thereby is inflated through a lumen internal to the sheath that has an opening into the interior annular space. In another embodiment, the annular space may be divided into separate inflatable lobes. In still another embodiment, the cuff member is a flexible and resilient member that is substantially toroidal in shape that is positioned on the outer surface of the sheath. In a further embodiment, the inflatable member is formed from an excess length of sheath cover material disposed on the disposable sheath. A single reentrant fold of sheath material is formed with an edge that is sealably and fixedly bonded to the sheath cover material to form an annular space capable of inflation. In alternate embodiments, the excess length of cover material may be used to form members with dual reentrant folds that comprise inflatable members with single and dual inflatable lobes.

64 Claims, 3 Drawing Sheets

US 6,461,294 B1

INFLATABLE MEMBER FOR AN ENDOSCOPE SHEATH

TECHNICAL FIELD

This invention relates generally to endoscopy, and more particularly to inflatable members attached to an endoscopic instrument.

BACKGROUND OF THE INVENTION

The use of endoscopes for diagnostic and therapeutic purposes is widespread. For example, there are upper endoscopes for examination of the esophagus, stomach and duodenum, colonoscopes for the examination of the colon, angioscopes for vascular examination, bronchoscopes for examining the bronchi, laparoscopes for examining the peritoneal cavity, and arthroscopes for the examination of joint spaces. The following discussion applies to all of these types of endoscopes.

An endoscope for examining the bronchial tract and conducting transbronchial biopsies is a good example of the usefulness of endoscopic technology. These devices, known as flexible fiber optic bronchoscopes, are widely used in diagnosing pulmonary diseases since they are capable of reaching the more distal bronchi in the bronchial tract. To properly navigate and view a bronchial area, the bronchoscope is generally structured to contain a fiber optic bundle within the elongated probe section. In addition to providing a direct viewing capability, flexible fiber optic bronchoscopes generally possess a means to remove tissue samples, or other material from the bronchial tract for biopsy or culture purposes. Tissue samples for biopsy purposes may be collected using a biopsy forceps extending from the distal end of the bronchoscope or by brushing the suspect area to capture cellular material for subsequent microscopic examination. Another commonly used technique to collect cellular material is to wash, or lavage the suspect area. When a lavage procedure is used, a saline solution is injected into the bronchial passage and subsequently withdrawn by suction through the distal end of the broncoscope to capture cellular material. Following withdrawal of the lavage fluid, the cellular material may be subjected to a cytological examination or culture.

One difficulty encountered in the use of endoscopes is continuously maintaining the endoscopic probe in a selected location within a body passage during the examination. Movement of the endoscopic probe while it is positioned within a body passage may occur for a number of reasons. For example, movement of the endoscope may occur due to an unintended bodily movement of the operator while the patient is undergoing the examination, or by an involuntary movement of the patient in response to the examination. Once the distal end of the endoscope has been dislodged from its intended location, it must be carefully repositioned before the examination may be resumed. Movement of the endoscope within a body passage is particularly pronounced during bronchoscopic examinations, since the patient must continue to breathe during the examination. Further, involuntary bronchospasmodic events within the bronchial passages may occur during the examination that will disrupt the location of the distal end of the bronchoscope. A significant additional difficulty resulting from unintended patient movement may arise when a biopsy procedure is conducted. Since a biopsy forceps or brush is generally used, an uncontrolled or unintended cutting of tissue in the passage due to patient movement may lead to hemoptysis. Moreover, since the biopsy forceps, or brush may reach and perforate the pleura, pneumothorax may also occur.

Still another difficulty encountered in the use of endoscopes for diagnostic purposes is the inability to sealably isolate a portion of the endoscope from the remainder of the body passage during an endoscopic examination. To facilitate internal viewing of a passage, for example, the fluid occupying the cavity is generally removed by means of a suction channel in the endoscope, which may be followed by the introduction of a gas through an additional channel in the endoscope to distend the internal space. Other endoscopic applications may require that a fluid be retained within the portion of the body passage that has been sealably isolated. For example, in transbronchial diagnostic procedures such as bronchoalveolar lavage, the bronchoscope is used to gently irrigate the air spaces in a distal air passage with a saline solution. Isolation of the saline to the region surrounding the distal end of the bronchoscope is required so that cellular samples removed during the lavage are sufficiently localized to be of diagnostic value. In particular, when collecting samples by lavage for use in the diagnosis of infectious pulmonary diseases, the sample must not be contaminated by bacterial or other agents transported to the distal end of the probe by the unrestrained movement of saline through the passages.

Increasingly, endoscopes are used with disposable sheaths that are positioned over the insertion tube of the endoscope to avoid the communication of disease from one patient to another. An additional advantage of the disposable sheath is that it allows the device to be used at more frequent intervals, since the need for lengthy cleaning and sterilization procedures is largely eliminated. Generally, the sheath is comprised of a flexible, thin, resilient elastomeric material, such as latex, that fits over and surrounds the insertion tube of the endoscope so the insertion tube is completely isolated from contaminants. The sheath is generally further comprised of a viewing window at the distal end, and may include a plurality of internal channels, or lumens, through which biopsy samples or fluids may be either introduced or removed. Accordingly, an additional difficulty encountered in the use of endoscopes concerns the incorporation of positioning and passage-blocking means into the disposable outer sheath.

Consequently, there exists a need in the art for an apparatus that will continuously maintain an endoscopic probe in a selected position within a body passage during the examination. In addition, the apparatus must be able to sealably close the passage to either retain fluids within a closed space, or to prevent a fluid from reoccupying the space during an examination. Finally, the apparatus must be compatible with disposable sheaths used with endoscopes.

SUMMARY OF THE INVENTION

The invention is directed towards apparatus and methods for attaching and forming enclosed inflatable members on an endoscope assembly with a disposable sheath. In one aspect, an apparatus in accordance with the invention includes a flexible and resilient cuff member that is positioned on the outer surface of the disposable sheath and sealably and fixedly bonded to the sheath cover material at the cuff edges to form an annular space capable of inflation. The inflatable member formed thereby is inflated through a lumen internal to the sheath that has an opening into the interior annular space. In another aspect, the annular space may be divided into separate inflatable lobes. In still another aspect, the cuff member is a flexible and resilient enclosed member that is substantially toroidal in shape that is positioned on the outer surface of the sheath. In a further aspect, the inflatable member is formed from an excess length of sheath cover material disposed on the disposable sheath. A single reentrant fold of sheath material is formed with an edge that is sealably and fixedly bonded to the sheath cover material to form an annular space capable of inflation. In alternate aspects, the excess length of cover material may be used to form members with dual reentrant folds that comprise inflatable members with single and dual inflatable lobes.

DETAILED DESCRIPTION OF THE INVENTION

Figure 1:
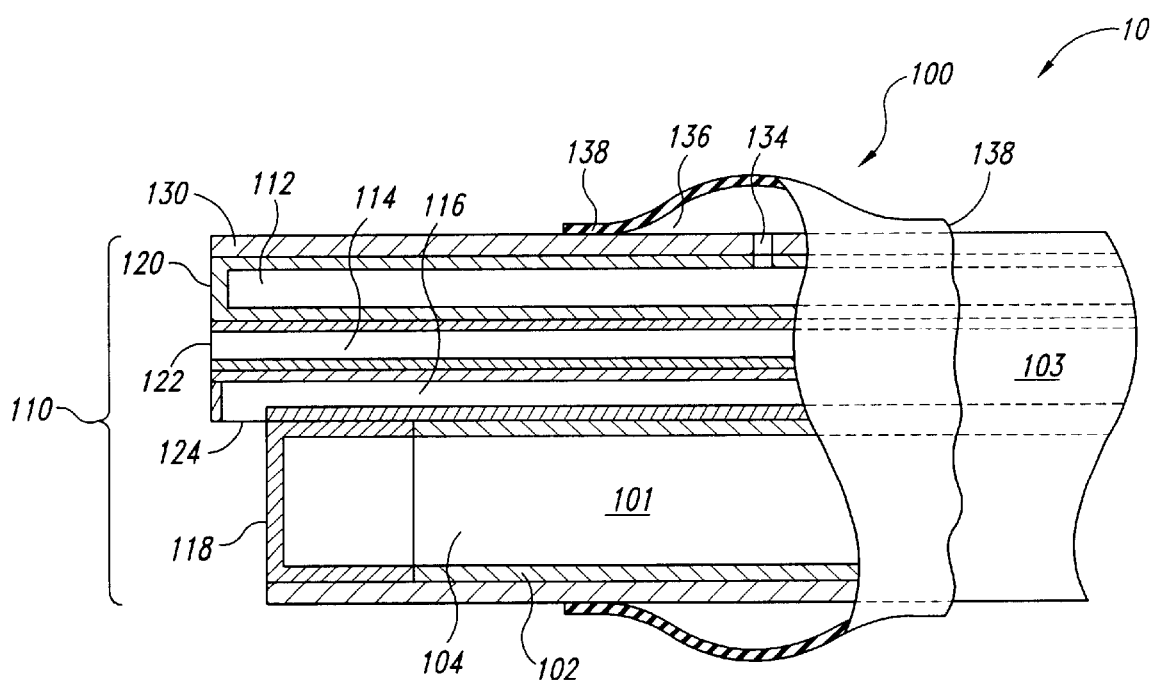
FIG. 1 is a partial cross-sectional view of an endoscope assembly with an inflatable cuff according to an embodiment of the invention.

The present invention is generally directed to inflatable members attached to an endoscope. Many of the specific details of certain embodiments of the invention are set forth in the following description and in FIGS. 1 through 6 to provide a thorough understanding of such embodiments. One skilled in the art will understand, however, that the present invention may have additional embodiments, or that the present invention may be practiced without several of the details described in the following description In the drawings, like reference numbers identify similar elements or steps. For ease in identifying the discussion of any particular element, the most significant digit in a reference number refers to the Figure number in which the element is first introduced (e.g., element 24 is first introduced and discussed with respect to FIG. 2). Further, it is understood that the inflatable members depicted in FIGS. 1 through 6 may assume a variety of sizes and shapes that depend on the amount of internal pressurization and/or the internal shape of a body cavity. Accordingly, for clarity of illustration, and to properly illustrate internal features of the various embodiments illustrated in FIGS. 1 through 6, the embodiments are shown at a generally intermediate stage of inflation.

FIG. 1 is a partial cross sectional view of an endoscope assembly 10 with a circumferentily disposed inflatable cuff 100 in accordance with an embodiment of the invention. As shown therein, the endoscope assembly 10 includes an insertion tube 101 positioned within a disposable endoscope sheath 103. The insertion tube 101 can have a variety of cross section shapes, such as circular, semicircular, etc., and is fabricated from a resilient material so that an insertion tube wall 102 may be flexed. The insertion tube 101 also has an internal space 104 that is structured to permit the illumination of tissue in internal passages, and to convey an image of the illuminated area from the distal end 110 of the endoscope to an external viewing device (not shown).

With reference still to FIG. 1, the endoscope sheath 103 has a transparent viewing lens 118 located at the distal end 110 of the disposable sheath 103 to allow the image to be conveyed to the external viewing device. The sheath 103 also has a plurality of internal lumens to accomplish specific tasks. For example, a lumen 124 may be provided to direct a flow of rinse water over the viewing lens 118 in order to rinse vision-impairing matter from the lens 118. A lumen 122 that is open at the distal end 110 may be used to capture a biopsy sample taken from the surrounding tissue area by means of an elongated forceps, or brush (not shown). Alternatively, the lumen 122 may be used to transfer a saline solution into a body passage during a lavage procedure. Further, the lumen 122 may also be used to transfer a compressed gas into a body passage in order to distend the passage for better optical viewing or biopsy sampling. An additional lumen 120 that is in fluid communication with a pressurized fluid source (not shown) is used to inflate an inflatable endoscope cuff 100, which will be described in greater detail below. The internal lumens 120, 122 and 124 are comprised of a resilient material to maintain flexibility of the sheath 103. The sheath 103 is covered with a flexible, resilient cover material 130 such as latex, polyvinylchloride, or polyurethane. Alternatively, other equally suitable materials for the cover material 130 are KRATON®, available from the GLS Corporation of McHenry, Ill, and C-FLEX®, available from Consolidated Polymer Technologies, Inc. of Largo, Fla.

Still referring to FIG. 1, an inflatable endoscope cuff 100 is comprised of a circular member positioned on the outer surface of the sheath 103. Although only a single inflatable cuff 100 is shown for clarity of illustration, it is understood that a plurality of cuffs 100 may be positioned along the length of the endoscope assembly 10, and that the plurality of cuffs 100 may be positioned at varying relative distances. The inflatable cuff 100 may be located at any location along the working length of the endoscope assembly 10, and forms a closed annular space 136 that is capable of inflation by a pressurized fluid. An opening 134 projects through the cover material 130 and through the wall of the lumen 120 to permit the pressurized fluid retained within the lumen 120 to enter the inflatable cuff 100. To retain the cuff 100 on the surface of the sheath 103, and to retain the pressurized fluid within the annular space 136, the cuff 100 is sealably fastened to the surface of the sheath 103 at the cuff edges 138 with a suitable adhesive placed between the cuff edge 138 and the cover material 130. An example of a suitable adhesive is cyanoacrylate, although other equivalent adhesives exist. Alternatively, the cuff edges 138 may be joined to the cover material 130 either by thermally fusing the cuff edges 138 to the cover material 130, or by wrapping lengths of surgical thread over the cuff edge 138 and securely tying the ends to sealably fasten the cuff edges 138 to the cover material 130.

The inflatable cuff 100 may be formed from latex, KRATON®, or C-FLEX®, although other suitable flexible and resilient materials may be used. For example, soft polyurethane may also be used. Preferably, the inflatable cuff 132 is formed from a flexible and resilient material with a thickness that ranges between 0.003 and 0.010 inches, with a durometer value of between approximately 30 and approximately 50.

Figure 2:
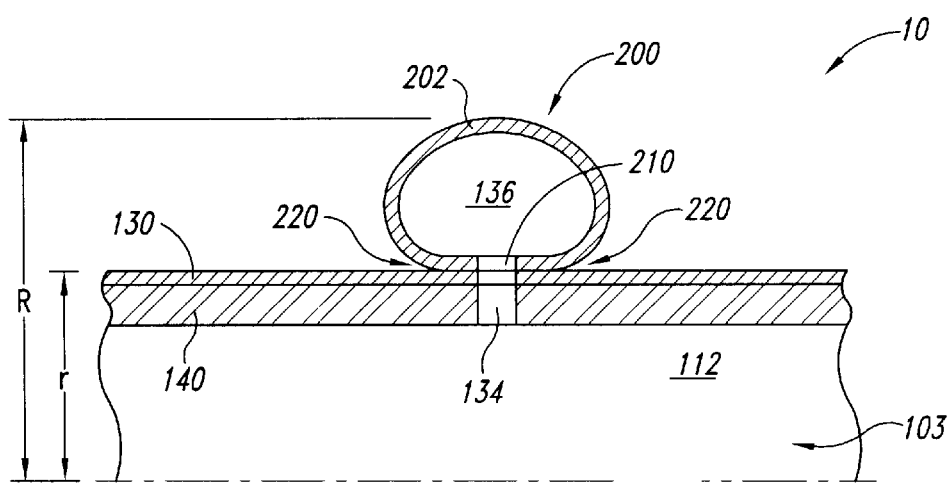
FIG. 2 is a cross-sectional view of an inflatable cuff according to another embodiment of the invention.

With reference now to FIG. 2, a partial cross sectional view of the endoscope assembly 10 with an alternative embodiment of an inflatable endoscope cuff 200 is shown. As shown therein, the inflatable endoscope cuff 200 is comprised of a resilient toroidally-shaped member 202 with an internal radius r and an external radius R. An opening 134 projects through the cover material 130 and through the wall of the lumen 120 to permit a pressurized fluid retained within the lumen interior space 112 to enter the inflatable member 202 through an opening 210 in the interior diameter of the member 202. To sealably retain the pressurized fluid within the annular space 136, the toroidally-shaped member 202 is sealably fastened to the surface of the sheath 103 at a location that is closely proximate to the opening 134. Moreover, to positionally retain the member 202 in the desired location on the surface of the sheath 103, it is preferable to join the interior diameter of the member 202 to the cover material 130 along a circumferential contact area 220 to ensure that the member 202 maintains its position on the endoscope assembly 10.

Figure 3:
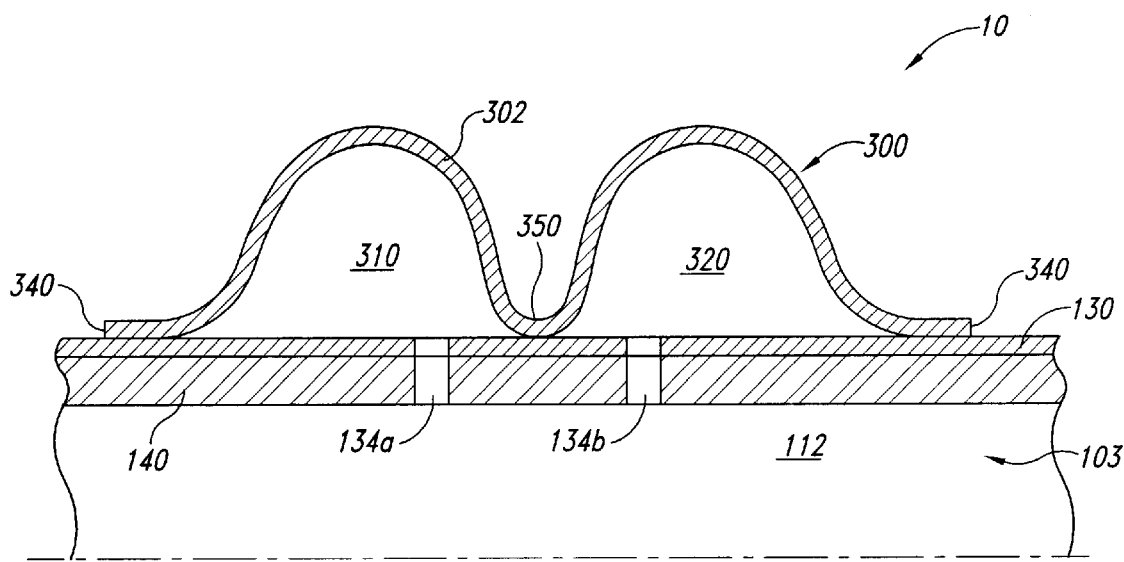
FIG. 3 is a cross-sectional view of an inflatable cuff according to still another embodiment of the invention.

FIG. 3 shows a partial cross sectional view of the endoscope assembly 10 with still another alternative embodiment of an inflatable endoscope cuff 300. As shown in FIG. 3, the inflatable endoscope cuff 300 is comprised of a resilient circular member 302 positioned on the outer surface of the sheath 103. In this embodiment, the length of the endoscope cuff 300 is sufficient to allow the formation of a pair of inflatable annular lobes 310 and 320 by attaching the circular member 302 to the cover material 130 at an approximate midpoint location 350 of the cuff 300. The development of an inflatable endoscope member with dual lobes is regarded as particularly advantageous since the dual lobes are regarded as more effective in conforming to irregular internal surfaces in body passages.

Still referring to FIG. 3, the cuff 300 may be retained at the midpoint location 350, and may be adhesively or thermally bonded to the cover material 130. Alternatively, the cuff may be attached to the cover material 130 at the mid point location 350 by a length of surgical thread wrapped around the cuff 300 that is securely knotted. To retain the pressurized fluid within the inflatable annular lobes 310 and 320, cuff edges 340 are sealably joined to the cover material 130 using an adhesive or thermal bonding method as previously described. Openings 134a and 134b project through the cover material 130 and through the lumen wall 140 to permit the pressurized fluid retained in the lumen interior space 112 to enter the lobes 310 and 320 during inflation.

Figure 4:
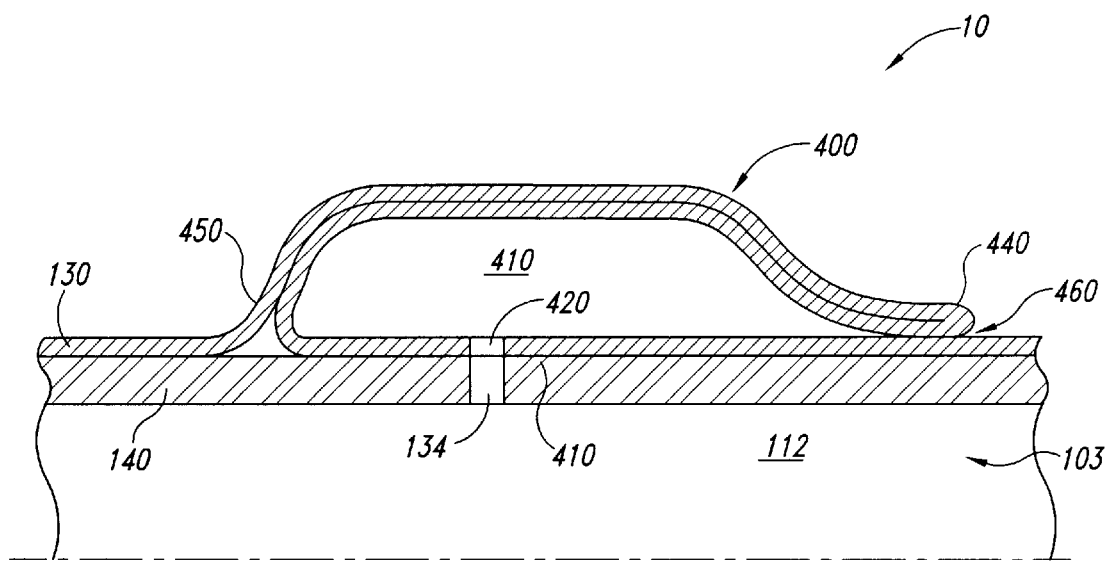
FIG. 4 is a cross-sectional view of an inflatable cuff according to yet another embodiment of the invention.

Turning now to FIG. 4, a partial cross sectional view of the endoscope assembly 10 with yet another alternative embodiment of an inflatable endoscope member 400 is shown. The endoscope assembly 10 according to this embodiment advantageously allows an inflatable member to be formed on the disposable sheath 103 without placing a separate circumferential member on the disposable sheath 103. The inflatable member 400 is formed by providing an excess length of the cover material 130 on the sheath 103 that may be drawn along the surface of the sheath 103 by an edge fold 440 that extends circumferentially around the sheath 103 to form a reentrant fold 450 in the cover material 130 that also extends circumferentially around the disposable sheath 103. The edge fold 440 is subsequently sealably attached to the cover material 130 at a surface location 460 to form a closed annular space 410 that is capable of being inflated. The sealable attachment between the edge fold 440 and the cover material 130 may be comprised of an adhesive or thermal bond. Alternatively, the attachment may be comprised of a length of surgical thread that is wrapped over the edge fold 440 and securely knotted. An opening 134 projects through the cover material 130 and through the wall of the lumen 120 to permit the pressurized fluid retained within the lumen interior space 112 to enter the inflatable annular member 400 during inflation. The member 400 may be sealably fastened to the surface of the sheath 103 at a location 410 that is closely proximate to the opening 134 to ensure that the lumen opening 134 in the lumen wall 140 remains in substantial alignment with the opening 420 through the cover material 130.

Figure 5:
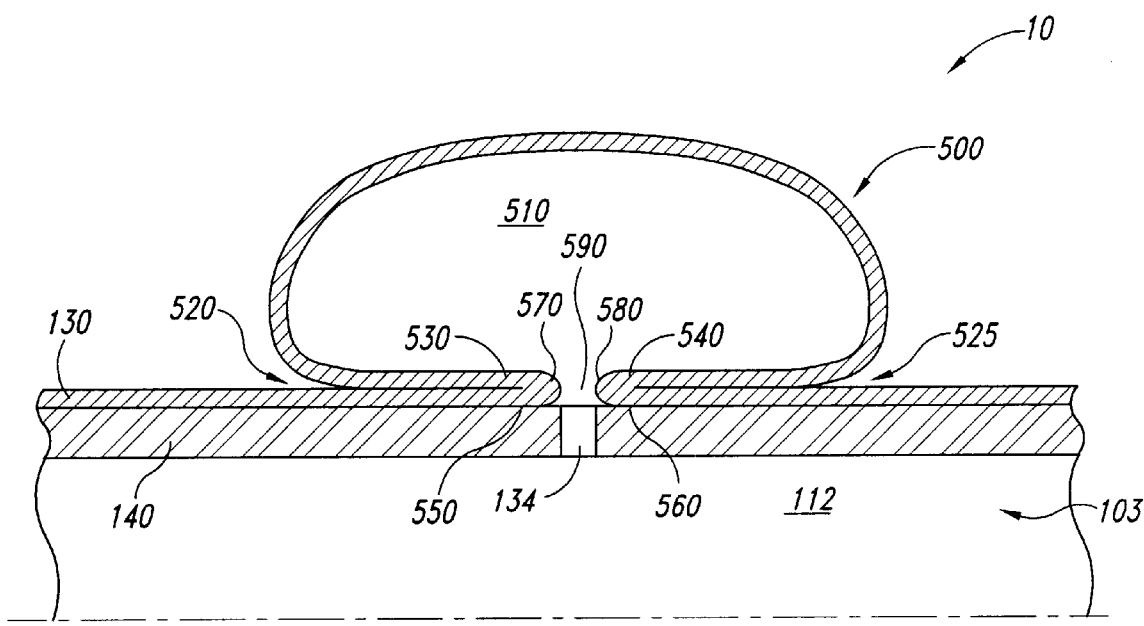
FIG. 5 is a cross-sectional view of an inflatable cuff according to another alternate embodiment of the invention.

FIG. 5 shows a partial cross sectional view of the endoscope assembly 10 with still another alternative embodiment of an inflatable endoscope member 500. As in the previous embodiment, the inflatable endoscope member 500 is advantageously formed from an excess length of the cover material 130 that is disposed on the sheath 103. As shown in FIG. 5, the excess length of the cover material 130 is drawn in a first direction along the surface of the sheath 103 to form a first reentrant fold 530 with a first edge fold 570. The first edge fold 570 is positioned approximately adjacent to the lumen opening 134. A second reentrant fold 540 is then formed in the cover material 130 by drawing the excess length in a second direction that is opposite to the first, to form a second edge fold 580 that is also positioned approximately adjacent to the lumen opening 134. When positioned approximately adjacent to the opening, the first edge fold 570 and the second edge fold 580 form an opening 590 into the inflatable enclosed annular space 510. The first and second reentrant folds 530 and 540 are sealably attached to the lumen wall 140 at locations 550 and 560 to ensure that the lumen opening 134 remains in substantial alignment with the opening 590. Adhesive or thermal bonding may form the sealable attachment at locations 550 and 560. As an alternative, surgical thread (not shown) may be inserted into the first reentrant fold 530 through the opening 520 and also inserted into the second reentrant fold 540 through the opening 525, both lengths of surgical thread being wrapped around the circumference of the disposable sheath 103 and securely knotted to retain the inflatable member 500 in position on the sheath 103.

Figure 6:
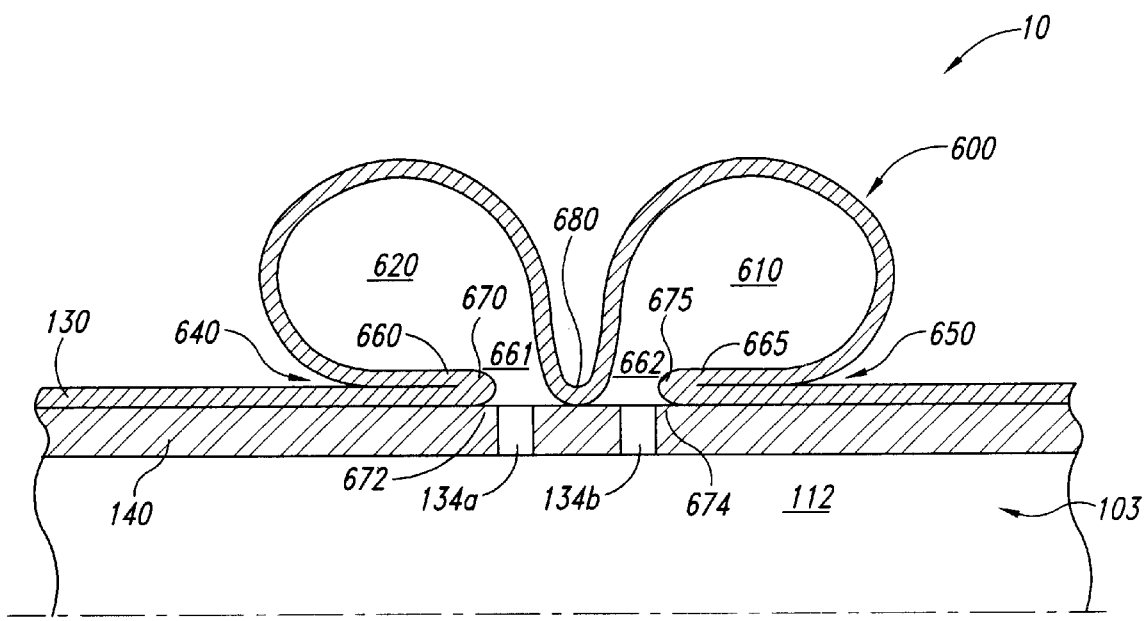
FIG. 6 is a cross-sectional view of an inflatable cuff according to still another alternate embodiment of the invention.

Turning now to FIG. 6, a partial cross sectional view of the endoscope assembly 10 with still another alternative embodiment of an inflatable endoscope member 600 is shown. The inflatable endoscope member 600 is similarly advantageously formed from an excess length of the cover material 130 that is disposed on the sheath 103. Drawing the excess length of cover material 130 along the surface of the sheath 103 in a first direction to form a first reentrant fold 660 with a first edge fold 670 forms the inflatable member 600. The first edge fold 670 is then positioned approximately adjacent to the opening 134a. Drawing the excess length in a second direction that is opposite to the first direction then forms a second reentrant fold 665 with a second edge fold 675. The second edge fold 675 is similarly positioned approximately adjacent to the opening 134b. The inflatable member 600 is divided into a pair of inflatable lobes 610 and 620 by attaching the cover material comprising the member 600 to the lumen wall 140 at an approximate midpoint location 680. The inflatable lobes 610 and 620 are inflated when pressurized fluid retained within the lumen interior space 112 enters the lobes through openings 134a and 134b. The first and second reentrant folds 660 and 665 are sealably attached to the lumen wall 140 at locations 672 and 674 to ensure that the lumen openings 134a and 134b remain in substantial alignment with the lobe entrances 661 and 662. As previously described, adhesive or thermal bonding may be used to form the sealable attachment at locations 672, 674 and 680. As an alternative, surgical thread (not shown) may be used to retain the position of the inflatable member on the sheath 103.

The above description of illustrated embodiments of the invention is not intended to be exhaustive or to limit the invention to the precise form disclosed. While specific embodiments of, and examples of, the invention are described in the foregoing for illustrative purposes, various equivalent modifications are possible within the scope of the invention, as those skilled in the relevant art will recognize.

Moreover, the various embodiments described above can be combined to provide further embodiments. For example, the various embodiments of the inflatable endoscope cuffs as previously described may be advantageously positioned along the length of the endoscope at uniform or varying distances to provide a plurality of inflatable cuffs along the length of the sheath. Further, different embodiments of the inflatable endoscope cuffs as previously described may be positioned at uniform or varying distances along the length of an endoscope to provide a plurality of different cuffs along the sheath to provide still further advantages. For example, the inflatable cuffs may be comprised of different materials or material thicknesses to obtain different inflation rates for the inflatable cuffs and/or different cuff volumes when the inflatable cuffs are inflated by the fluid passage. Accordingly, the invention is not limited by the disclosure, but instead the scope of the invention is to be determined entirely by the following claims.

What is claimed is:

1. An endoscope assembly for insertion into an internal passage in a human patient, comprising:
    an elongated flexible insertion tube;
    a fluid impermeable flexible sheath having a distal end and positioned over the insertion tube;
    a fluid passage adapted to communicate a fluid and extending through the flexible sheath to define at least one opening in the flexible sheath; and
    at least one circumferential radially expandable flexible member positioned on the flexible sheath and sealably attached to the flexible sheath to form an enclosed inflatable annular space in fluid communication with the at least one opening.

2. The endoscope assembly according to claim 1 wherein the flexible member is further comprised of a substantially resilient material.

3. The endoscope assembly according to claim 1 wherein the fluid passage is further comprised of a lumen extending from the opening in the flexible sheath to a source of pressurized fluid.

4. The endoscope assembly according to claim 1 wherein the flexible member is further comprised of a reentrant fold in the flexible sheath to form a circumferential flap with a circumferential base adjoining the flexible insertion tube and a circumferential edge disposed away from the base, the flap extending over the opening in the flexible sheath and the edge being sealably attached to the flexible sheath.

5. The endoscope assembly according to claim 1 wherein the flexible member is further comprised of a first reentrant fold in the flexible sheath to form a first circumferential edge and a second reentrant fold in the flexible sheath to form a second circumferential edge, the first and second edges substantially abutting the opening and sealably attached to the flexible sheath proximate to the opening to form an enclosed space capable of inflation.

6. The endoscope assembly according to claim 1 wherein the opening in the flexible sheath comprises a plurality of openings and wherein the flexible member is further comprised of a first reentrant fold in the flexible sheath to form a first circumferential edge and a second reentrant fold in the flexible sheath to form a second circumferential edge, the first and second edges sealably attached to the flexible sheath proximate to the openings, the flexible member being further sealably attached to the flexible sheath at a position intermediate between the first and second circumferential edges to form a pair of enclosed annular spaces, each space being in fluid communication with at least one of the plurality of openings.

7. The endoscope assembly according to claim 1 wherein the flexible member is further comprised of an annular ring of a flexible material with an inner face and an outer face, the inner face being substantially in facial contact with the flexible sheath when not inflated, and the outer face being disposed away from the flexible sheath and having first and second peripheral edges which are sealably attached to the sheath.

8. The endoscope assembly according to claim 1 wherein the flexible member is further comprised of a toroidally-shaped member with an inner circumference and an outer circumference, the inner circumference being in facial contact with the flexible sheath, and the outer circumference being disposed away from the sheath, the inner circumference having an opening positioned over the first opening in the flexible sheath and being sealably attached to the sheath at the inner circumference.

9. The endoscope assembly according to claim 1 wherein the opening in the flexible sheath comprises a plurality of openings and wherein the flexible member is further comprised of an annular ring of a flexible material with an inner face and an outer face, the inner face being substantially in facial contact with the flexible sheath when not inflated, and the outer face being disposed away from the flexible sheath and having first and second peripheral edges which are sealably attached to the sheath, the inner face being further sealably attached to the flexible sheath at a position intermediate between the first and second peripheral edges to form a pair of enclosed annular spaces, each space being in fluid communication with at least one of the plurality of openings.

10. The endoscope assembly according to claim 1 wherein the flexible member is further comprised of a silicone rubber.

11. The endoscope assembly according to claim 1 wherein the flexible member is further comprised of a polyurethane material.

12. The endoscope assembly according to claim 1 wherein the flexible member is further comprised of a latex rubber.

13. The endoscope assembly according to claim 1 wherein the flexible member is further comprised of an elastomer with a durometer value of between approximately 30 and 50.

14. The endoscope assembly according to claim 1 wherein the flexible member is comprised of KRATON®.

15. The endoscope assembly according to claim 1 wherein the flexible member is comprised of C-FLEX®.

16. The endoscope assembly according to claim 1 wherein the flexible member is comprised of polyvinylchloride.

17. The endoscope assembly according to claim 1 wherein the flexible member is comprised of a material with a thickness of approximately about 0.003 inches to approximately about 0.010 inches.

18. The endoscope assembly according to claim 1 wherein the flexible member is sealably attached to the flexible sheath with an adhesive.

19. The endoscope assembly according to claim 18 wherein the adhesive is cyanoacrylate.

20. The endoscope assembly according to claim 1 wherein the flexible member is sealably attached to the flexible sheath by thermal fusion.

21. The endoscope assembly according to claim 1 wherein the flexible member is sealably attached to the flexible sheath with surgical thread.

22. In an endoscope having an elongated flexible insertion tube, a disposable sheath, comprising:
    a fluid impermeable flexible sheath having a distal end and adapted to be positioned over the insertion tube;

a fluid passage to communicate a fluid and extending through the flexible sheath to define at least one opening in the flexible sheath; and a circumferential radially expandable flexible member positioned on the flexible sheath and sealably attached to the flexible sheath to form an enclosed inflatable annular space in fluid communication with the at least one opening.

23. The disposable sheath according to claim 22 wherein the flexible member is further comprised of a substantially resilient material.

24. The disposable sheath according to claim 22 wherein the fluid passage is further comprised of a lumen extending from the opening in the flexible sheath to a source of pressurized fluid.

25. The disposable sheath according to claim 22 wherein the flexible member is further comprised of a reentrant fold in the flexible sheath to form a circumferential flap with a circumferential base adjoining the flexible insertion tube and a circumferential edge disposed away from the base, the flap extending over the opening in the flexible sheath and the edge being sealably attached to the flexible sheath.

26. The disposable sheath according to claim 22 wherein the flexible member is further comprised of a first reentrant fold in the flexible sheath to form a first circumferential edge and a second reentrant fold in the flexible sheath to form a second circumferential edge, the first and second edges substantially abutting the opening and sealably attached to the flexible sheath proximate to the opening to form an enclosed space capable of inflation.

27. The disposable sheath according to claim 22 wherein the opening in the flexible sheath comprises a plurality of openings and wherein the flexible member is further comprised of a first reentrant fold in the flexible sheath to form a first circumferential edge and a second reentrant fold in the flexible sheath to form a second circumferential edge, the first and second edges sealably attached to the flexible sheath proximate to the openings, the flexible member being further sealably attached to the flexible sheath at a position intermediate between the first and second circumferential edges to form a pair of enclosed annular spaces, each space being in fluid communication with at least one of the plurality of openings.

28. The disposable sheath according to claim 22 wherein the flexible member is further comprised of an annular ring of a flexible material with an inner face and an outer face, the inner face being substantially in facial contact with the flexible sheath when not inflated, and the outer face being disposed away from the flexible sheath and having first and second peripheral edges which are sealably attached to the sheath.

29. The disposable sheath according to claim 22 wherein the flexible member is further comprised of a toroidally-shaped member with an inner circumference and an outer circumference, the inner circumference being in facial contact with the flexible sheath, and the outer circumference being disposed away from the sheath, the inner circumference having an opening positioned over the first opening in the flexible sheath and being sealably attached to the sheath at the inner circumference.

30. The disposable sheath according to claim 22 wherein the opening in the flexible sheath comprises a plurality of openings and wherein the flexible member is further comprised of an annular ring of a flexible material with an inner face and an outer face, the inner face being substantially in facial contact with the flexible sheath when not inflated, and the outer face being disposed away from the flexible sheath and having first and second peripheral edges which are sealably attached to the sheath, the inner face being further sealably attached to the flexible sheath at a position intermediate between the first and second peripheral edges to form a pair of enclosed annular spaces, each space being in fluid communication with at least one of the plurality of openings.

31. The disposable sheath according to claim 22 wherein the flexible member is further comprised of a silicone rubber.

32. The disposable sheath according to claim 22 wherein the flexible member is further comprised of a polyurethane material.

33. The disposable sheath according to claim 22 wherein the flexible member is further comprised of a latex rubber.

34. The disposable sheath according to claim 22 wherein the flexible member is further comprised of an elastomer with a durometer value of between approximately 30 and 50.

35. The disposable sheath according to claim 22 wherein the flexible member is comprised of KRATON®.

36. The disposable sheath according to claim 22 wherein the flexible member is comprised of C-FLEX®.

37. The disposable sheath according to claim 22 wherein the flexible member is comprised of polyvinylchloride.

38. The disposable sheath according to claim 22 wherein the flexible member is comprised of a material with a thickness of approximately about 0.003 inches to approximately about 0.010 inches.

39. The disposable sheath according to claim 22 wherein the flexible member is sealably attached to the flexible sheath with an adhesive.

40. The disposable sheath according to claim 39 wherein the adhesive is cyanoacrylate.

41. The disposable sheath according to claim 22 wherein the flexible member is sealably attached to the flexible sheath by thermal fusion.

42. The disposable sheath according to claim 22 wherein the flexible member is sealably attached to the flexible sheath with surgical thread.

43. A method of forming a circumferential radially expandable flexible member on an insertion tube of an endoscope assembly, comprising:

drawing a fluid impermeable flexible sheath over a surface of an elongated flexible insertion tube;

forming a fluid passage that extends through the flexible sheath to define at least one opening in the sheath; and forming a circumferential radially expandable flexible member in fluid communication with the at least one opening in the flexible sheath to define an enclosed annular space adapted to be inflated.

44. The method according to claim 43 wherein the step of forming a fluid passage further comprises forming a lumen extending from the opening in the flexible sheath to the source of pressurized fluid.

45. The method according to claim 43 wherein the step of forming a flexible member further comprises forming a reentrant fold in the flexible sheath to form a circumferential flap having a circumferential edge disposed away from the insertion tube, extending the flap over the opening in the sheath, and sealably joining the circumferential edge to the flexible sheath to form an enclosed annular space in fluid communication with the opening.

46. The method according to claim 43 wherein the step of forming a flexible member is further comprised of a first reentrant fold in the flexible sheath to form a first circumferential edge and a second reentrant fold in the flexible sheath to form a second circumferential edge, the first and second edges substantially abutting the opening and sealably attached to the flexible sheath proximate to the opening.

47. A method of using an endoscope with a flexible sheath to visually examine an internal passage in a human patient, comprising:

positioning a flexible sheath having a circumferential radially expandable member over the insertion tube of the endoscope;

inserting the insertion tube of the endoscope with the flexible sheath positioned thereon into a passage in the human body;

locating a region within the passage to be viewed endoscopically;

circumferentially expanding a localized region of the sheath extending circumferentially around the periphery of the sheath to substantially lock the endoscope proximate to the region; and viewing the region.

48. The method according to claim 47 wherein the step of viewing further comprises viewing the region using a fiber optic device.

49. The method according to claim 47 wherein the step of viewing further comprises viewing the region using a camera.

50. The method according to claim 47 wherein the step of circumferentially expanding a localized region of the sheath further comprises sealably isolating the cavity.

51. A method of using an endoscope with a flexible sheath to extract cellular material from an internal passage in a human patient, comprising:

positioning a flexible sheath having a circumferential radially expandable member over the insertion tube of the endoscope;

inserting the insertion tube of the endoscope with the flexible sheath positioned thereon into a passage in the human body;

locating a region within the passage from which cellular material is to be removed;

circumferentially expanding a localized region of the sheath extending circumferentially around the periphery of the sheath to substantially lock the endoscope proximate to the region; and removing the cellular material from the region.

52. The method according to claim 51 wherein the step of removing cellular material is further comprised of removing cellular material by a lavage procedure.

53. The method according to claim 51 wherein the step of removing cellular material is further comprised of removing cellular material with an elongated forceps that is extended along the insertion length of the endoscope.

54. The method according to claim 51 wherein the step of removing cellular material is further comprised of removing cellular material with a brush that is extended along the insertion length of the endoscope.

55. The method according to claim 51 wherein the step of circumferentially expanding a localized region of the sheath further comprises sealably isolating the cavity.

56. The endoscope assembly of claim 1 wherein the circumferential radially expandable flexible member is comprised of a circumferential radially expandable flexible member positioned substantially proximate to the distal end of the flexible sheath.

57. The endoscope of claim 22 wherein the circumferential radially expandable flexible member is comprised of a circumferential radially expandable flexible member positioned substantially proximate to the distal end of the flexible sheath.

58. The endoscope assembly of claim 1 wherein the opening in the flexible sheath is proximate to the distal end of the flexible sheath.

59. An endoscope having an elongated flexible insertion tube, a disposable sheath, comprising:

a fluid impermeable flexible sheath having a distal end and structured to be positioned over the insertion tube;

a fluid passage structured to communicate a fluid, the passage extending through the insertion tube and having a plurality of openings projecting through the flexible sheath; and a plurality of radially expandable flexible members positioned on the flexible sheath, each member being spaced apart from the other members and each member being sealably attached to the flexible sheath to form an enclosed annular inflatable space in fluid communication with at least one of the plurality of openings.

60. The disposable sheath according to claim 59 wherein the plurality of flexible members is further comprised of a substantially resilient material having a material thickness.

61. The disposable sheath according to claim 59 wherein the plurality of flexible members is further comprised of a plurality of non-uniformly spaced apart flexible members.

62. The disposable sheath according to claim 60 wherein at least one of the plurality of flexible members is comprised of a resilient material having a material thickness that substantially differs from the material thickness of the other flexible members.

63. The disposable sheath according to claim 60 wherein at least one of the plurality of flexible members is comprised of a resilient material that differs from the material comprising the other flexible members.

64. The disposable sheath according to claim 59 wherein the fluid passage is further comprised of a lumen in fluid communication with each opening in the flexible sheath and fluidly coupled to a source of pressurized fluid.

* * * * *